(12) United States Patent
Kubo et al.

(10) Patent No.: US 7,501,289 B2
(45) Date of Patent: Mar. 10, 2009

(54) BIOSENSOR

(75) Inventors: Toshiaki Kubo, Kanagawa (JP);
Toshihide Ezoe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 246 days.

(21) Appl. No.: 11/020,254

(22) Filed: Dec. 27, 2004

(65) Prior Publication Data

US 2005/0158850 A1    Jul. 21, 2005

(30) Foreign Application Priority Data

Dec. 25, 2003  (JP) ............................. 2003-429860
Mar. 26, 2004  (JP) ............................. 2004-093048
Mar. 26, 2004  (JP) ............................. 2004-093049
Apr. 27, 2004  (JP) ............................. 2004-130593

(51) Int. Cl.
*G01N 33/543* (2006.01)

(52) U.S. Cl. .................. 436/518; 422/82.11; 427/2.11; 427/2.13; 427/163.2; 427/337; 427/338; 427/402; 427/404; 427/414; 435/287.1; 435/287.2; 436/524; 436/525; 436/805

(58) Field of Classification Search ............. 422/82.11; 435/287.1, 287.2; 436/518, 524, 525, 805; 427/2.11, 2.13, 163.2, 337, 338, 402, 404, 427/414
See application file for complete search history.

(56) References Cited

U.S. PATENT DOCUMENTS

| 5,242,828 | A  | * | 9/1993 | Bergstrom et al. ....... 435/287.1 |
| 6,180,288 | B1 | * | 1/2001 | Everhart et al. ................ 430/2 |
| 6,444,254 | B1 |   | 9/2002 | Chilkoti et al. |
| 6,984,485 | B2 | * | 1/2006 | Matson .......................... 435/4 |
| 2003/0194715 | A1 | | 10/2003 | Li et al. |

FOREIGN PATENT DOCUMENTS

| JP | 11-006834 A | 1/1999 |
| JP | 2003-075448 A | 3/2003 |
| JP | 2003-194820 A | 7/2003 |
| JP | 2003-215029 A | 7/2003 |
| JP | 2003-525429 A | 8/2003 |
| JP | 2003-294610 A | 10/2003 |

* cited by examiner

*Primary Examiner*—Christopher L Chin
(74) *Attorney, Agent, or Firm*—Sughrue Mion, PLLC

(57) ABSTRACT

It is an object of the present invention to provide a biosensor, which is not significantly affected by the baseline fluctuation and suppresses nonspecific adsorption. The present invention provides a biosensor, which comprises a metal surface or metal film coated with a hydrophobic polymer, and has two or more types of different surfaces in a region coated with a hydrophobic polymer.

11 Claims, 1 Drawing Sheet

US 7,501,289 B2

BIOSENSOR

TECHNICAL FIELD

The present invention relates to a biosensor and a method for analyzing an interaction between biomolecules using the biosensor. Particularly, the present invention relates to a biosensor which is used for a surface plasmon resonance biosensor and a method for analyzing an interaction between biomolecules using the biosensor.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The QCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences.

In all of the above-described techniques, the surface where a physiologically active substance is immobilized is important. Surface plasmon resonance (SPR), which is most commonly used in this technical field, will be described below as an example.

A commonly used measurement chip comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules.

As a thin film having a functional group capable of immobilizing a physiologically active substance, there has been reported a measurement chip where a physiologically active substance is immobilized by using a functional group binding to metal, a linker with a chain length of 10 or more atoms, and a compound having a functional group capable of binding to the physiologically active substance (Japanese Patent No. 2815120). Moreover, a measurement chip comprising a metal film and a plasma-polymerized film formed on the metal film has been reported (Japanese Patent Laid-Open No. 9-264843).

With regard to the aforementioned chip, the original activity of a physiologically active substance may be decreased by immobilization of the substance on a surface. Thus, only physiologically active substances that are strong against immobilization have been used as test materials. In addition, it has been pointed out that an excessive amount of carboxylic acid exists on the surface and that a physiologically active substance becomes inactivated due to the effects of such carboxylic acid. Under such circumstances, a surface capable of stably immobilizing all types of physiologically active substances has been desired for examining the relationship with enzyme activity and the like.

When a specific binding reaction between a physiologically active substance and a test substance is measured, the test substance is not necessarily comprised of a single component. There may also be a case where a test substance is required to be measured in a heterogeneous system such as a cell extract. In such a case, if contaminants such as various proteins or lipids are adsorbed on the detection surface nonspecifically, measurement/detection sensitivity is significantly reduced. The fact that nonspecific adsorption is highly likely to occur on the above detection surface has been problematic. In order to solve such problems, several methods have been studied. For example, a method of immobilizing a hydrophilic hydrogel on a metal surface via a linker, so as to repress physical adsorption, has been used (Japanese Patent No. 2815120, U.S. Pat. No. 5,436,161, and Japanese Patent Laid-Open No. 8-193948). However, nonspecific adsorption has not been sufficiently controlled by this method.

On the other hand, with regard to the aforementioned biosensor, in order to eliminate the influence of disturbance on measurement (e.g. temperature change, concentration change, or pressure change) so as to reduce baseline fluctuation, it is preferable that a measurement unit for measuring the specific binding reaction between a physiologically active substance and a test substance and a reference unit that does not carry out such a binding reaction exist on a single plane and be as adjacent as possible to each other. Thus, it becomes necessary that a reference unit coexist with a measurement unit on the surface of an SPR sensor of a thin polymer film.

U.S. Pat. No. 6,444,254 describes a method for microstamping a biological ligand on the surface of a polymer, which comprises; forming on the polymer surface a first functional group by a method selected from the group consisting of hydrolysis, reduction, photoinduced graft polymerization, amination, polyethylene oxide surface cross polymerization, the chemical reaction of a terminal hydroxyl group, corona discharge, plasma etching, lasing, and ion beam treatment; allowing a stamp, on which a biological ligand having at least a second functional group is adsorbed, to come into contact with the surface of the first functional group, so as to form a covalent bond between the biological ligand and the first functional group on the polymer surface; and then separating the stamp from the polymer surface, so as to directly immobilize the biochemical ligand on the polymer surface via such a covalent bond. In the aforementioned method, a solid (PDMS) is allowed to come into contact with a polymer film for patterning. However, since a sensor used for SPR has a surface formed by attaching a thin polymer film on a thin metal film, it has little physical strength. Contact with a solid injures the surface of the sensor, and thus, the aforementioned method is not suitable for SPR.

DISCLOSURE OF INVENTION

It is an object of the present invention to solve the aforementioned problems. In other words, it is an object of the present invention to provide a biosensor, which is not significantly affected by the baseline fluctuation and suppresses nonspecific adsorption. That is to say, it is an object of the present invention to provide a detection surface used for biosensors, which is capable of immobilizing all types of physiologically active substances stably, that is, while suppressing decreases in the original activities of the physiologically active substances. It is another object of the present invention to provide a biosensor: which can favorably detect the binding of a physiologically active substance with a substance interacting therewith even when the physiologically active substance is immobilized on the biosensor using a solution containing a low concentration of the physiologically active substance; and which causes a low variation in the binding amount of the physiologically substance and in the binding amount of the substance interacting therewith.

As a result of intensive studies directed towards achieving the aforementioned objects, the present inventors have found that a desired biosensor can be provided by establishing at least two types of surfaces on a single plane of a biosensor that suppresses nonspecific adsorption by coating the surface of a substrate thereof with a hydrophobic polymer, thereby completing the present invention. In addition, they have found that a hydrophilic compound is allowed to bind to the surface of a substrate coated with a hydrophobic polymer, so as to stably immobilize a physiologically active substance thereon (that is, while suppressing a decrease in the activity of the physiologically active substance), thereby completing the present invention. Moreover, they have found that a desired biosensor can be provided by patterning at least two types of surfaces by ink-jet printing in a region coated with a hydrophobic polymer in a biosensor that suppresses nonspecific absorption by coating the surface of a substrate thereof with the hydrophobic polymer, thereby completing the present invention.

Thus, the present invention provides a biosensor, which comprises a metal surface or metal film coated with a hydrophobic polymer, and has two or more types of different surfaces in a region coated with a hydrophobic polymer.

Preferably, at least a measurement unit to which a physiologically active substance or a substance interacting therewith binds and a measurement unit that does not have a physiologically active substance or a substance interacting therewith exit on a single plane.

Preferably, the metal surface or metal film consists of a free electron metal selected from the group consisting of gold, silver, copper, platinum, and aluminum.

Preferably, wherein the thickness of the metal film is between 1 angstrom and 5,000 angstroms.

Preferably, the coating thickness of the hydrophobic polymer is between 1 angstrom and 5,000 angstroms.

Preferably, the biosensor of the present invention is used in non-electrochemical detection, and more preferably in surface plasmon resonance analysis.

Preferably, the biosensor is formed in a measurement chip that is used for a surface plasmon resonance measurement device comprising a dielectric block, a metal film formed on one side of the dielectric block, a light source for generating a light beam, an optical system for allowing said light beam to enter said dielectric block so that total reflection conditions can be obtained at the interface between said dielectric block and said metal film and so that various incidence angles can be included, and a light-detecting means for detecting the state of surface plasmon resonance by measuring the intensity of the light beam totally reflected at said interface, wherein said measurement chip is basically composed of said dielectric block and said metal film, wherein said dielectric block is formed as a block including all of an incidence face and an exit face for said light beam and a face on which said metal film is formed, and wherein said metal film is unified with this dielectric block.

Another aspect of the present invention provides a method for producing the biosensor according to the present invention, which comprises steps of coating a substrate with a hydrophobic polymer, and producing two or more types of surfaces on a single plane without allowing a solid to come into contact with a detection region.

Preferably, at least two types of surfaces are produced on a single plane using a diaphragm(s).

Another aspect of the present invention provides a method for immobilizing a physiologically active substance on a biosensor, which comprises a step of allowing a physiologically active substance to come into contact with the biosensor according to the present invention, so as to allow said physiologically active substance to bind to the surface of said biosensor via a covalent bond.

Another aspect of the present invention provides a method for detecting or measuring a substance interacting with a physiologically active substance, which comprises a step of allowing a test substance to come into contact with the biosensor according to the present invention to the surface of which the physiologically active substance binds via a covalent bond.

Preferably, the substance interacting with the physiologically active substance is detected or measured by a non-electrochemical method.

Preferably, the substance interacting with the physiologically active substance is detected or measured by surface plasmon resonance analysis.

Another aspect of the present invention provides a biosensor comprising a substrate which is coated with a hydrophobic polymer, to the surface of which a hydrophilic compound binds.

Preferably, the molecular weight of the hydrophilic compound is between 50 and 20,000.

Preferably, one group binding to one molecule of the physiologically active substance exists in one molecule of the hydrophilic compound.

Preferably, 2 to 1,000 groups binding to a physiologically active substance exist in one molecule of the hydrophilic compound.

Preferably, the hydrophilic compound is gelatin, alginic acid, chitosan, dextran, polyvinyl alcohol, polyethylene glycol or a derivative thereof, carrageenan, agarose, polyacrylic acid, or polyacrylamide.

Another aspect of the present invention provides a method for producing the biosensor according to the present invention, which comprises steps of coating a substrate with a hydrophobic polymer, and allowing a hydrophilic compound to bind to the hydrophobic polymer coated on the substrate.

Another aspect of the present invention provides the biosensor according to the present invention, wherein a physiologically active substance is bound to the surface by covalent bonding.

Another aspect of the present invention provides a method for immobilizing a physiologically active substance on a biosensor, which comprises a step of allowing a physiologically active substance to come into contact with the biosensor according to the present invention, so as to allow said physiologically active substance to bind to the surface of said biosensor via a covalent bond.

Another aspect of the present invention provides a method for detecting or measuring a substance interacting with a physiologically active substance, which comprises a step of allowing a test substance to come into contact with the biosensor according to the present invention to the surface of which the physiologically active substance binds via a covalent bond.

Preferably, the substance interacting with the physiologically active substance is detected or measured by a non-electrochemical method.

Preferably, the substance interacting with the physiologically active substance is detected or measured by surface plasmon resonance analysis.

Another aspect of the present invention provides a biosensor comprising a substrate coated with a hydrophobic polymer, wherein at least two types of surfaces are patterned in a region coated with a hydrophobic polymer by ink-jet printing.

Preferably, at least one type of linker is patterned on the surface of the substrate coated with the hydrophobic polymer.

Preferably, the linker is represented by the formula (1):

$$X-L-Y \quad \text{Formula (1):}$$

wherein X represents a group capable of reacting with a functional group of the hydrophobic polymer, L represents a bivalent linking group, and Y represents a group capable of immobilizing a physiologically active substance.

Preferably, a physiologically active substance is bound to the surface by covalent bonding.

Preferably, at least a measurement unit to which a physiologically active substance or a substance interacting therewith binds and a measurement unit that does not have a physiologically active substance or a substance interacting therewith exit on a single plane.

Another aspect of the present invention provides a method for immobilizing a physiologically active substance on a biosensor, which comprises a step of allowing a physiologically active substance to come into contact with the biosensor according to the present invention, so as to allow said physiologically active substance to bind to the surface of said biosensor via a covalent bond.

Another aspect of the present invention provides a method for detecting or measuring a substance interacting with a physiologically active substance, which comprises a step of allowing a test substance to come into contact with the biosensor according to the present invention to the surface of which the physiologically active substance binds via a covalent bond.

Preferably, the substance interacting with the physiologically active substance is detected or measured by a non-electrochemical method.

Preferably, the substance interacting with the physiologically active substance is detected or measured by surface plasmon resonance analysis.

BEST MODE FOR CARRYING OUT THE INVENTION

Figure 1:
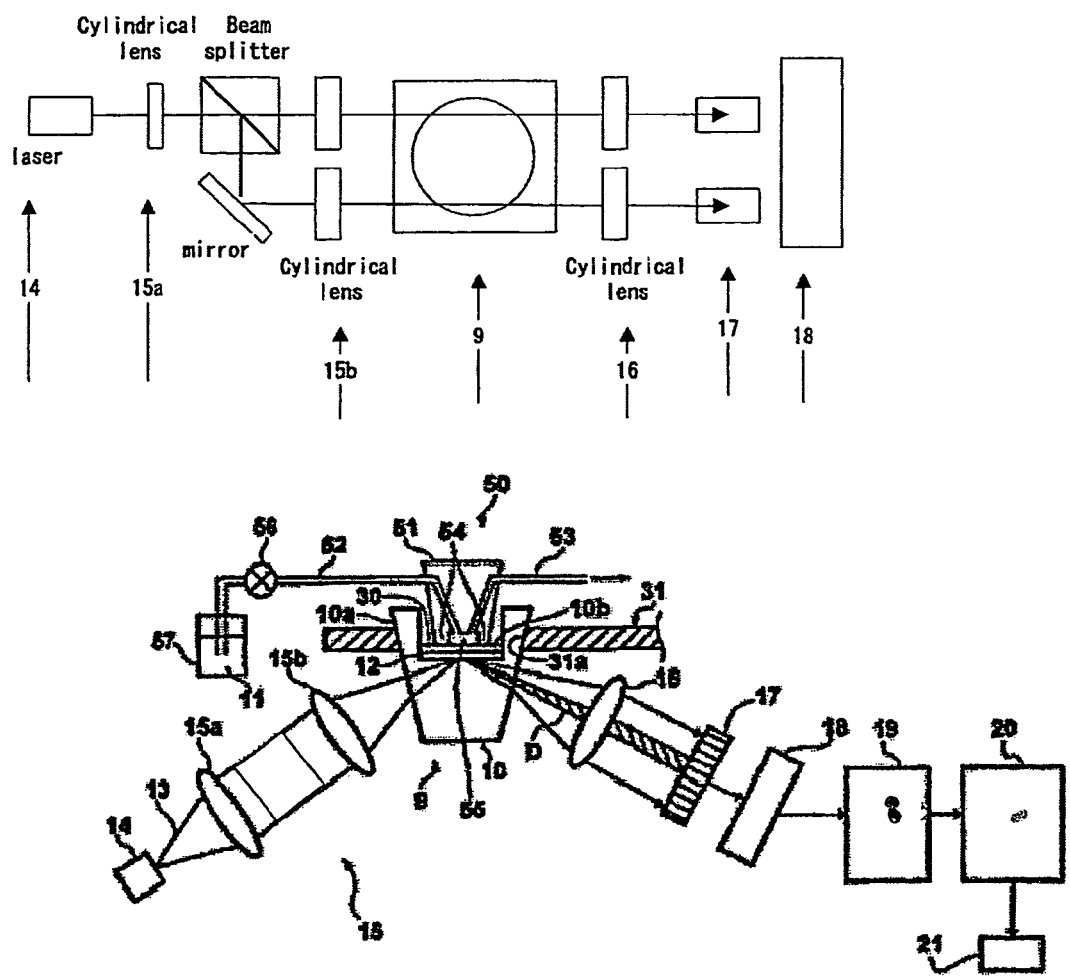
FIG. 1 shows the surface plasmon resonance measurement device used in the examples. In the figure, 9 represents measurement chip, 10 represents dielectric block, 10a represents sample-retaining unit, 10b represents interface, 11 represents liquid sample, 12 represents metal film, 13 represents light beam, 14 represents laser light source, 15 represents optical system, 15a represents collimator lens, 15b represents condenser, 16 represents collimator lens, 17 represents photodiode array, 18 represents differential amplifier array, 19 represents driver, 20 represents signal processing unit, 21 represents display unit, 30 represents sensing substance, 31 represents table, 31a represents chip-retaining pore, 50 represents flow channel unit, 51 represents flow channel holder, 52 represents feeding path, 53 represents discharging path, 54 represents sealing unit, 55 represents measurement flow channel, 56 represents pomp, and 57 represents liquid storage unit.

The embodiments of the present invention will be described below.

The biosensor of the present invention is characterized in that it comprise a metal surface or metal film coated with a hydrophobic polymer, and has two or more types of different surfaces in a region coated with a hydrophobic polymer.

When two or more types of surfaces are located on a single plane in the present invention, it is preferable to adopt a method wherein a solid does not come into contact with a detection region. Specific examples of such a method may include a method for preparing a droplet at the tip of a syringe and allowing only the droplet to come into contact with a detection region, a method for spraying a droplet from a nozzle, a method for preparing a flow channel and passing a reaction solution through the flow channel, and a method for establishing a diaphragm(s) and filling the insides with liquids. Of these, the method of using a diaphragm(s) is particularly preferable.

An example of such at least two types of surfaces located on a single plane may be a combination of a measurement unit to which a physiologically active substance or a substance interacting therewith binds and a reference unit having neither a physiologically active substance nor a substance interacting therewith. With regard to a measurement unit, it is also possible to establish a plurality of measurement units by using different substances as substances to be bound.

In the present invention, it becomes possible to cancel the baseline fluctuation caused by disturbance by establishing a measurement unit and a reference unit on a single plane as described above, thereby substantially stabilizing immobilization. In addition, it becomes also possible to suppress non-specific adsorption by adopting a method wherein a solid does not come into contact with a detection region, so as to establish a measurement unit and a reference unit. Conventional methods have not simultaneously achieved both decrease in the baseline fluctuation and suppression of non-specific adsorption. Thus, such effects have been achieved by the present invention for the first time.

The biosensor of the present invention has as broad a meaning as possible, and the term biosensor is used herein to mean a sensor, which converts an interaction between biomolecules into a signal such as an electric signal, so as to measure or detect a target substance. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/coenzyme, antigen/antibody, or hormone/receptor. The biosensor operates on the principle that a substance having an affinity with another substance, as described above, is immobilized on a substrate to be used as a molecule-recognizing substance, so that the corresponding substance can be selectively measured.

The hydrophobic polymer used in the present invention is a polymer having no water-absorbing properties. Its solubility in water (at 25° C.) is 10% or less, more preferably 1% or less, and most preferably 0.1% or less.

A hydrophobic monomer which forms a hydrophobic polymer can be selected from vinyl esters, acrylic esters, methacrylic esters, olefins, styrenes, crotonic esters, itaconic diesters, maleic diesters, fumaric diesters, allyl compounds, vinyl ethers, vinyl ketones, or the like. The hydrophobic polymer may be either a homopolymer consisting of one type of monomer, or copolymer consisting of two or more types of monomers.

Examples of a hydrophobic polymer that is preferably used in the present invention may include polystyrene, polyethylene, polypropylene, polyethylene terephthalate, polyvinyl chloride, polymethyl methacrylate, polyester, and nylon.

A substrate is coated with a hydrophobic polymer according to common methods. Examples of such a coating method may include spin coating, air knife coating, bar coating, blade coating, slide coating, curtain coating, spray method, evaporation method, cast method, and dip method.

In the dip method, coating is carried out by contacting a substrate with a solution of a hydrophobic polymer, and then with a liquid which does not contain the hydrophobic polymer. Preferably, the solvent of the solution of a hydrophobic polymer is the same as that of the liquid which does not contain said hydrophobic polymer.

In the dip method, a layer of a hydrophobic polymer having an uniform coating thickness can be obtained on a surface of a substrate regardless of inequalities, curvature and shape of the substrate by suitably selecting a coating solvent for hydrophobic polymer.

The type of coating solvent used in the dip method is not particularly limited, and any solvent can be used so long as it can dissolve a part of a hydrophobic polymer. Examples thereof include formamide solvents such as N,N-dimethylformamide, nitrile solvents such as acetonitrile, alcohol solvents such as phenoxyethanol, ketone solvents such as 2-butanone, and benzene solvents such as -toluene, but are not limited thereto.

In the solution of a hydrophobic polymer which is contacted with a substrate, the hydrophobic polymer may be dissolved completely, or alternatively, the solution may be a suspension which contains undissolved component of the hydrophobic polymer. The temperature of the solution is not particularly limited, so long as the state of the solution allows a part of the hydrophobic polymer to be dissolved. The temperature is preferably −20° C. to 100° C. The temperature of the solution may be changed during the period when the substrate is contacted with a solution of a hydrophobic polymer. The concentration of the hydrophobic polymer in the solution is not particularly limited, and is preferably 0.01% to 30%, and more preferably 0.1% to 10%.

The period for contacting the solid substrate with a solution of a hydrophobic polymer is not particularly limited, and is preferably 1 second to 24 hours, and more preferably 3 seconds to 1 hour.

As the liquid which does not contain the hydrophobic polymer, it is preferred that the difference between the SP value (unit: $(J/cm^3)^{1/2}$) of the solvent itself and the SP value of the hydrophobic polymer is 1 to 20, and more preferably 3 to 15. The SP value is represented by a square root of intermolecular cohesive energy density, and is referred to as solubility parameter. In the present invention, the SP value d was calculated by the following formula. As the cohesive energy (Ecoh) of each functional group and the mol volume (V), those defined by Fedors were used (R. F. Fedors Polym.Eng-.Sci. 14(2), P147,P472(1974)).

$$\Delta = (SEcoh/SV)^{1/2}$$

Examples of the SP values of the hydrophobic polymers and the solvents are shown below;

Solvent: 2-phenoxyethanol: 25.3 against polymethylmethacrylate-polystyrene copolymer (1:1): 21.0

Solvent:acetonitrile: 22.9 against polymethylmethacrylate: 20.3

Solvent:toluene: 18.7 against polystyrene: 21.6

The period for contacting a substrate with a liquid which does not contain the hydrophobic polymer is not particularly limited, and is preferably 1 second to 24 hours, and more preferably 3 seconds to 1 hour. The temperature of the liquid is not particularly limited, so long as the solvent is in a liquid state, and is preferably −20° C. to 100° C. The temperature of the liquid may be changed during the period when the substrate is contacted with the solvent. When a less volatile solvent is used, the less volatile solvent may be substituted with a volatile solvent which can be dissolved in each other after the substrate is contacted with the less volatile solvent, for the purpose of removing the less volatile solvent.

The coating thickness of a hydrophobic polymer is not particularly limited, but it is preferably between 1 angstrom and 5,000 angstroms, and particularly preferably between 10 angstroms and 3,000 angstroms.

Preferably, the metal surface or metal film of the biosensor of the present invention is coated with a hydrophobic polymer. A metal constituting the metal surface or metal film is not particularly limited, as long as surface plasmon resonance is generated when the metal is used for a surface plasmon resonance biosensor. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 1 angstrom and 5,000 angstroms, and particularly preferably between 10 angstroms and 2,000 angstroms. If the thickness exceeds 5,000 angstroms, the surface plasmon phenomenon of a medium cannot be sufficiently detected. Moreover, when an interstitial layer consisting of chrome or the like is provided, the thickness of the interstitial layer is preferably between 1 angstrom and 100 angstroms.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and having excellent workability are preferably used.

In another aspect of the present invention, there is provided a biosensor comprising a substrate which is coated with a hydrophobic polymer, to the surface of which a hydrophilic compound binds.

The hydrophilic compound used in the present invention is explained.

The term "hydrophilic" is used herein to mean a compound that is soluble at an amount of 5 g or greater in 100 g of water. Examples of such a compound may include gelatin, alginic acid, chitosan, dextran, polyvinyl alcohol, polyethylene glycol, carrageenan, agarose, polyacrylic acid, and polyacrylamide. Of these, polyethylene glycol is preferably used.

A hydrophilic compound used in the present invention is preferably a compound having a molecular weight between 50 and 30,000. A compound having a molecular weight between 50 and 20,000 is more preferable, and a compound having a molecular weight between 100 and 10,000 is particularly preferable. Further, a compound having a molecular weight between 100 and 1,500 is more preferable.

The hydrophilic compound used in the present invention preferably has one group capable of immobilizing one physiologically active substance per molecule. In addition, the present hydrophilic compound preferably has a group reacting with the surface of a biosensor other than the aforementioned binding group. However, it may also be possible that one group binding to one physiologically active substance be introduced onto the surface of the biosensor after the physiologically active substance has been bound to the surface thereof.

Alternatively, the hydrophilic compound used in the present invention preferably has 2 to 1,000 groups capable of immobilizing a physiologically active substance per molecule, and more preferably has 2 to 100 groups capable of immobilizing a physiologically active substance per molecule. In addition, the present hydrophilic compound preferably has a group reacting with the surface of a biosensor, other than the aforementioned binding groups. However, it may also be possible that one group binding to a physiologically active substance be introduced onto the surface of the biosensor after the physiologically active substance has been bound to the surface thereof.

The group reacting with the surface of a biosensor is preferably a halogen atom, an amino group, an amino group protected with a protecting group, a carboxyl group, a carboxyl group having a leaving group, a hydroxyl group, a hydroxyl group protected with a protecting group, an aldehyde group, —NHNH$_2$, —N=C=O, —N=C=S, an epoxy group, or a vinyl group.

A protecting group is used herein to mean a group capable of forming a functional group by deprotecting the above group in a reaction system. For example, protecting groups of an amino group may include a tert-butyloxycarbonyl group (Boc), a 9-fluorenylmethyloxycarbonyl group (Fmoc), a nitrophenylsulfenyl group (Nps), and a dithiasuccinyl group (Dts).

An acyl group is an example of a protecting group of a hydroxyl group.

Examples of a leaving group used herein may include a halogen atom, an alkoxy group, an aryloxy group, an alkylcarbonyloxy group, an arylcarbonyloxy group, a halogenated alkylcarbonyloxy group, an alkylsulfonyloxy group, a halogenated alkylsulfonyloxy group, and arylsulfonyloxy group.

In addition, an ester group generated by combining carboxylic acid, a known dehydrating condensing reagent (e.g., carbodiimides) and an N-hydroxy compound is preferably used as a leaving group.

The group capable of immobilizing a physiologically active substance represents a group capable of immobilizing a physiologically active substance, or a group capable of binding to a compound capable of binding to a physiologically active substance, and is preferably a halogen atom, an amino group, an amino group protected with a protecting group, a carboxyl group, a carboxyl group having a leaving group, a hydroxyl group, a hydroxyl group protected with a protecting group, an aldehyde group, —NHNH$_2$, —N=C=O, —N=C=S, an epoxy group, and a vinyl group.

The same above groups can be used herein as protecting groups and leaving groups.

Specific examples of the hydrophilic compound that can be used in the present invention are given below, but examples are not limited thereto.

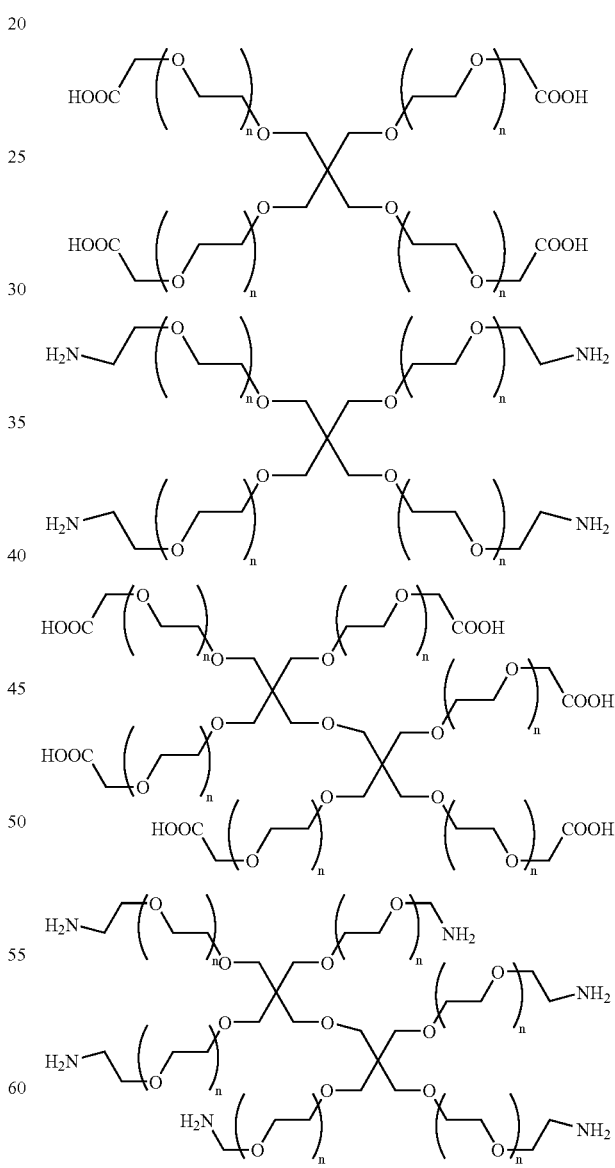

-continued

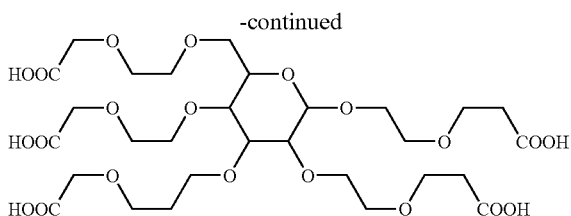

In another embodiment, the biosensor of the present invention is characterized in that it comprises a substrate coated with a hydrophobic polymer, and that at least two types of surfaces are patterned in a region coated with a hydrophobic polymer by ink-jet printing.

In the present invention, at least two types of surfaces are patterned on the surface of a biosensor coated with a hydrophobic polymer by ink-jet printing. Such patterning is carried out to achieve the following purposes:

(1) A portion on which a physiologically active substance is immobilized and a portion on which a physiologically active substance is not immobilized are patterned.

(2) At least two types of physiologically active substances are immobilized by patterning.

Patterning of the surface of a film by ink-jet printing can be applied at any stage of the process of immobilizing a physiologically active substance on the surface of a hydrophobic polymer film, but it is preferably performed at the stage of introducing a linker for immobilizing the physiologically active substance.

In the present invention, ink-jet recording methods are not limited, and known methods are used. Examples of such a known method may include: a charge control method of using electrostatic induction to discharge ink; a drop-on-demand method (pressure pulse method) of using pressure caused by vibration of piezo elements; an acoustic ink-jet method comprising changing an electric signal into an acoustic beam, applying the acoustic beam to ink, and discharging the ink using radiation pressure; and a thermal ink-jet method (bubble-jet (registered trade mark)) comprising heating ink to form air bubbles and using the generated pressure.

Such ink-jet recording methods may also include a method of ejecting a large amount of ink having a low concentration known as "photoink" in a small volume, a method of improving image quality using a plurality of inks, which substantially have the same hue but different concentrations, and a method of using water-clear ink. The volume in which ink droplets are ejected is mainly controlled by a print head.

For example, in the case of the thermal ink-jet method, the volume in which ink droplets are ejected can be controlled by the structure of a print head. That is to say, ink having a desired size can be ejected by changing the size of an ink chamber, heating unit, or nozzle. In addition, even in the thermal ink-jet method, it is also possible to eject droplets with different sizes by establishing multiple print heads having heating units or nozzles with different sizes.

In the case of the drop-on-demand method of using piezo elements, it is possible to change the volume in which ink droplets are ejected by the structure of a print head, as in the case of the thermal ink-jet method. However, as described later, it is also possible to control the waveform of a driving signal that drives piezo elements, so as to eject droplets with different sizes even using print heads having the same structure.

An example of such at least two types of surfaces located on a single plane may be a combination of a measurement unit to which a physiologically active substance or a substance interacting therewith binds, and a reference unit having neither a physiologically active substance nor a substance interacting therewith. With regard to measurement units, it is also possible to establish a plurality of measurement units by using different substances as substances to be bound.

In the present invention, it becomes possible to cancel the baseline fluctuation caused by disturbance by establishing a measurement unit and a reference unit on a single plane as described above, thereby substantially stabilizing immobilization.

The biosensor of the present invention comprising a substrate coated with a hydrophobic polymer preferably has a functional group capable of immobilizing a physiologically active substance on the outermost surface of the substrate. The term "the outermost surface of the substrate" is used to mean "the surface, which is farthest from the substrate," and more specifically, it means "the surface of a hydrophobic polymer applied on a substrate, which is farthest from the substrate."

Examples of a preferred functional group may include —OH, —SH, —COOH, —NR$^1$R$^2$ (wherein each of R$^1$ and R$^2$ independently represents a hydrogen atom or lower alkyl group), —CHO, —NR$^3$NR$^1$R$^2$ (wherein each of R$^1$, R$^2$ and R$^3$ independently represents a hydrogen atom or lower alkyl group), —NCO, —NCS, an epoxy group, and a vinyl group. The number of carbon atoms contained in the lower alkyl group is not particularly limited herein. However, it is generally about C1 to C10, and preferably C1 to C6.

In order to introduce these functional groups into the outermost surface, a method is applied that involves applying a hydrophobic polymer containing a precursor of such a functional group on a metal surface or metal film, and then generating the functional group from the precursor located on the outermost surface by chemical treatment. For example, polymethyl methacrylate, a hydrophobic polymer containing —COOCH$_3$ group is applied on a metal film, and then the surface comes into contact with an NaOH aqueous solution (1N) at 40° C. for 16 hours, so that a —COOH group is generated on the outermost surface.

A physiologically active substance is covalently bound to the above-obtained surface for a biosensor via the above functional group, so that the physiologically active substance can be immobilized on the metal surface or metal film.

In a preferred embodiment of the present invention, at least one type of linker is patterned on the surface of a substrate coated with a hydrophobic polymer. A linker used in the present invention will be described below.

The linker used in the present invention means a linker capable of indirectly immobilizing a physiologically active substance and a hydrophobic polymer. Examples of an immobilization method may include a method using an electrostatic interaction, a method using a hydrophobic interaction, and a method using chemical bonds. Among these, a method using chemical bonds is preferably used. Examples of such chemical bonds may include covalent bonds, ion bonds, coordinate bonds and hydrogen bonds. Of these, covalent bonds are most preferably used.

A compound represented by the following formula (1) is a specific example of the linker used in the present invention:

X-L-Y       Formula (1):

wherein X represents a group capable of reacting with a functional group of a hydrophobic polymer, L represents a bivalent linking group, and Y represents a group capable of immobilizing a physiologically active substance.

In the above formula (1), X represents a group capable of reacting with a functional group of a hydrophobic polymer, and it is preferably a halogen atom, an amino group, an amino group protected with a protecting group, a carboxyl group, a carboxyl group having a leaving group, a hydroxyl group, a hydroxyl group protected with a protecting group, an aldehyde group, —NHNH$_2$, —N=C=O, —N=C=S, an epoxy group, or a vinyl group.

A protecting group is used herein to mean a group capable of forming a functional group by deprotecting the above group in a reaction system. For example, protecting groups of an amino group may include a tert-butyloxycarbonyl group (Boc), a 9-fluorenylmethyloxycarbonyl group (Fmoc), a nitrophenylsulfenyl group (Nps), and a dithiasuccinyl group (Dts).

An acyl group is an example of a protecting group of a hydroxyl group.

Examples of a leaving group used herein may include a halogen atom, an alkoxy group, an aryloxy group, an alkylcarbonyloxy group, an arylcarbonyloxy group, a halogenated alkylcarbonyloxy group, an alkylsulfonyloxy group, a halogenated alkylsulfonyloxy group, and arylsulfonyloxy group.

In addition, an ester group generated by combining carboxylic acid, a known dehydrating condensing reagent (e.g., carbodiimides) and an N-hydroxy compound is preferably used as a leaving group.

In the formula (1), L represents a bivalent linking group. The total number of atoms of L is preferably 2 to 1000. Moreover, L is preferably one selected from a group consisting of a substituted or unsubstituted alkyl group, a substituted or unsubstituted alkyleneoxy group, a substituted or unsubstituted aryleneoxy group, and a bivalent binding group in which X in the formula (1) is bound to Y in another molecule, so that the structure is connected to another structure.

In the formula (1), Y represents a group capable of immobilizing a physiologically active substance, and it is preferably a halogen atom, an amino group, an amino group protected with a protecting group, a carboxyl group, a carboxyl group having a leaving group, a hydroxyl group, a hydroxyl group protected with a protecting group, an aldehyde group, —NHNH$_2$, —N=C=O, —N=C=S, an epoxy group, or a vinyl group.

The same above groups can be used herein as protecting groups and leaving groups.

Specific examples of a compound represented by the formula (1) are given below. However, compounds represented by the formula (1), which can be used in the present invention, are not limited thereto.

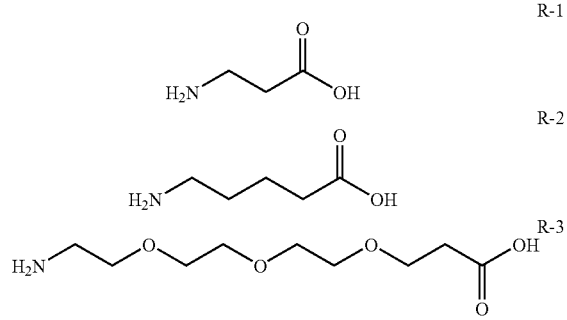

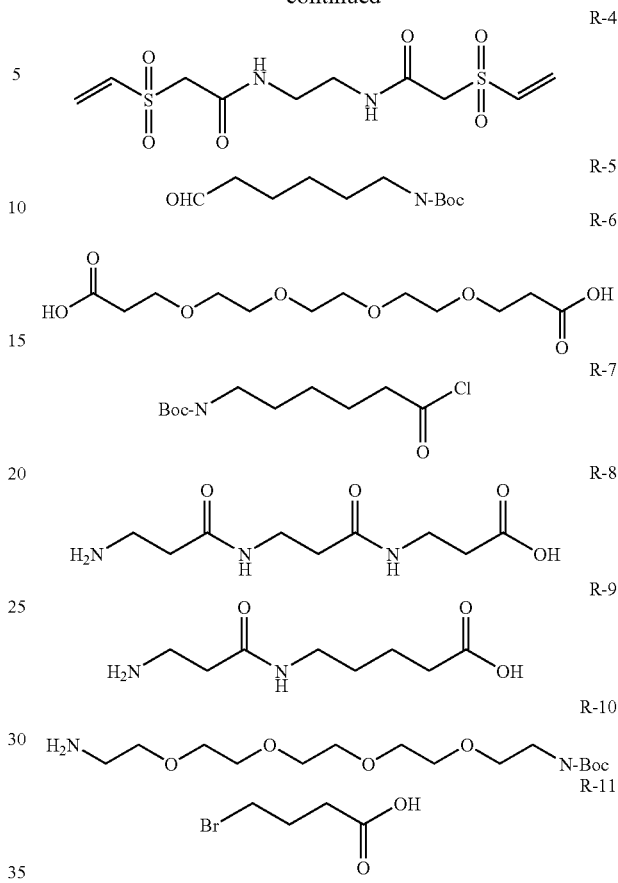

The biosensor of the present invention can be produced by the process of applying a linker to a substrate coated with a hydrophobic polymer by ink-jet printing and allowing them to react with each other. It is preferable that the thus produced biosensor have a linker on the outermost surface of the substrate thereof, and that the linker have a group capable of immobilizing a physiologically active substance. The term "the outermost surface of the substrate" is used herein to mean "the surface, which is farthest from the substrate," and more specifically, it means "the surface, which is farthest from the surface in a hydrophobic polymer applied on a substrate."

A physiologically active substance immobilized on the surface for the biosensor of the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against O antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

When a physiologically active substance is a protein such as an antibody or enzyme or nucleic acid, an amino group, thiol group or the like of the physiologically active substance is covalently bound to a functional group located on a metal surface, so that the physiologically active substance can be immobilized on the metal surface.

A biosensor to which a physiologically active substance is immobilized as described above can be used to detect and/or measure a substance which interacts with the physiologically active substance.

Thus, the present invention provides a method of detecting and/or measuring a substance interacting with the physiologically active substance immobilized to the biosensor of the present invention, to which a physiologically active substance is immobilized, wherein the biosensor is contacted with a test substance As such a test substance, for example, a sample containing the above substance interacting with the physiologically active substance can be used.

In the present invention, it is preferable to detect and/or measure an interaction between a physiologically active substance immobilized on the surface used for a biosensor and a test substance by a nonelectric chemical method. Examples of a non-electrochemical method may include a surface plasmon resonance (SPR) measurement technique, a quartz crystal microbalance (QCM) measurement technique, and a measurement technique that uses functional surfaces ranging from gold colloid particles to ultra-fine particles.

In a preferred embodiment of the present invention, the biosensor of the present invention can be used as a biosensor for surface plasmon resonance which is characterized in that it comprises a metal film placed on a transparent substrate.

A biosensor for surface plasmon resonance is a biosensor used for a surface plasmon resonance biosensor, meaning a member comprising a portion for transmitting and reflecting light emitted from the sensor and a portion for immobilizing a physiologically active substance. It may be fixed to the main body of the sensor or may be detachable.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light.

A device using a system known as the Kretschmann configuration is an example of a surface plasmon measurement device for analyzing the properties of a substance to be measured using a phenomenon whereby a surface plasmon is excited with a lightwave (for example, Japanese Patent Laid-Open No. 6-167443). The surface plasmon measurement device using the above system basically comprises a dielectric block formed in a prism state, a metal film that is formed on a face of the dielectric block and comes into contact with a measured substance such as a sample solution, a light source for generating a light beam, an optical system for allowing the above light beam to enter the dielectric block at various angles so that total reflection conditions can be obtained at the interface between the dielectric block and the metal film, and a light-detecting means for detecting the state of surface plasmon resonance, that is, the state of attenuated total reflection, by measuring the intensity of the light beam totally reflected at the above interface.

The biosensor of the present invention can preferably be formed in a measurement chip used for a surface plasmon resonance measurement device comprising a dielectric block, a metal film formed on one side of the dielectric block, a light source for generating a light beam, an optical system for allowing the above light beam to enter the above dielectric block so that total reflection conditions can be obtained at the interface between the dielectric block and the metal film and so that various incidence angles can be included, and a light-detecting means for detecting the state of surface plasmon resonance by measuring the intensity of the light beam totally reflected at the above interface. The aforementioned measurement chip is basically composed of the above dielectric block and the above metal film, wherein the above dielectric block is formed as a block including all of an incidence face and an exit face for the above light beam and a face on which the above metal film is formed, and wherein the above metal film is unified with this dielectric block.

In order to achieve various incident angles as described above, a relatively thin light beam may be caused to enter the above interface while changing an incident angle. Otherwise, a relatively thick light beam may be caused to enter the above interface in a state of convergent light or divergent light, so that the light beam contains components that have entered therein at various angles. In the former case, the light beam whose reflection angle changes depending on the change of the incident angle of the entered light beam can be detected with a small photodetector moving in synchronization with the change of the above reflection angle, or it can also be detected with an area sensor extending along the direction in which the reflection angle is changed. In the latter case, the light beam can be detected with an area sensor extending to a direction capable of receiving all the light beams reflected at various reflection angles.

With regard to a surface plasmon measurement device with the above structure, if a light beam is allowed to enter the metal film at a specific incident angle greater than or equal to a total reflection angle, then an evanescent wave having an electric distribution appears in a measured substance that is in contact with the metal film, and a surface plasmon is excited by this evanescent wave at the interface between the metal film and the measured substance. When the wave vector of the evanescent light is the same as that of a surface plasmon and thus their wave numbers match, they are in a resonance state, and light energy transfers to the surface plasmon. Accordingly, the intensity of totally reflected light is sharply decreased at the interface between the dielectric block and the metal film. This decrease in light intensity is generally detected as a dark line by the above light-detecting means. The above resonance takes place only when the incident beam is p-polarized light. Accordingly, it is necessary to set the light beam in advance such that it enters as p-polarized light.

If the wave number of a surface plasmon is determined from an incident angle causing the attenuated total reflection (ATR), that is, an attenuated total reflection angle ($\theta SP$), the dielectric constant of a measured substance can be determined. As described in Japanese Patent Laid-Open No. 11-326194, a light-detecting means in the form of an array is considered to be used for the above type of surface plasmon measurement device in order to measure the attenuated total reflection angle ($\theta SP$) with high precision and in a large dynamic range. This light-detecting means comprises multiple photo acceptance units that are arranged in a certain direction, that is, a direction in which different photo acceptance units receive the components of light beams that are totally reflected at various reflection angles at the above interface.

In the above case, there is established a differentiating means for differentiating a photodetection signal outputted from each photo acceptance unit in the above array-form light-detecting means with regard to the direction in which the photo acceptance unit is arranged. An attenuated total reflection angle ($\theta SP$) is then specified based on the derivative value outputted from the differentiating means, so that properties associated with the refractive index of a measured substance are determined in many cases.

In addition, a leaking mode measurement device described in "Bunko Kenkyu (Spectral Studies)" Vol. 47, No. 1 (1998), pp. 21 to 23 and 26 to 27 has also been known as an example of measurement devices similar to the -above-described device using attenuated total reflection (ATR). This leaking mode measurement device basically comprises a dielectric block formed in a prism state, a clad layer that is formed on a face of the dielectric block, a light wave guide layer that is formed on the clad layer and comes into contact with a sample solution, a light source for generating a light beam, an optical system for allowing the above light beam to enter the dielectric block at various angles so that total reflection conditions can be obtained at the interface between the dielectric block and the clad layer, and a light-detecting means for detecting the excitation state of waveguide mode, that is, the state of attenuated total reflection, by measuring the intensity of the light beam totally reflected at the above interface.

In the leaking mode measurement device with the above structure, if a light beam is caused to enter the clad layer via the dielectric block at an incident angle greater than or equal to a total reflection angle, only light having a specific wave number that has entered at a specific incident angle is transmitted in a waveguide mode into the light wave guide layer, after the light beam has penetrated the clad layer. Thus, when the waveguide mode is excited, almost all forms of incident light are taken into the light wave guide layer, and thereby the state of attenuated total reflection occurs, in which the intensity of the totally reflected light is sharply decreased at the above interface. Since the wave number of a waveguide light depends on the refractive index of a measured substance placed on the light wave guide layer, the refractive index of the measurement substance or the properties of the measured substance associated therewith can be analyzed by determining the above specific incident angle causing the attenuated total reflection.

In this leaking mode measurement device also, the above-described array-form light-detecting means can be used to detect the position of a dark line generated in a reflected light due to attenuated total reflection. In addition, the above-described differentiating means can also be applied in combination with the above means.

The above-described surface plasmon measurement device or leaking mode measurement device may be used in random screening to discover a specific substance binding to a desired sensing substance in the field of research for development of new drugs or the like. In this case, a sensing substance is immobilized as the above-described measured substance on the above thin film layer (which is a metal film in the case of a surface plasmon measurement device, and is a clad layer and a light guide wave layer in the case of a leaking mode measurement device), and a sample solution obtained by dissolving various types of test substance in a solvent is added to the sensing substance. Thereafter, the above-described attenuated total reflection angle ($\theta SP$) is measured periodically when a certain period of time has elapsed.

If the test substance contained in the sample solution is bound to the sensing substance, the refractive index of the sensing substance is changed by this binding over time. Accordingly, the above attenuated total reflection angle ($\theta SP$) is measured periodically after the elapse of a certain time, and it is determined whether or not a change has occurred in the above attenuated total reflection angle ($\theta SP$), so that a binding state between the test substance and the sensing substance is measured. Based on the results, it can be determined whether or not the test substance is a specific substance binding to the sensing substance. Examples of such a combination between a specific substance and a sensing substance may include an antigen and an antibody, and an antibody and an antibody. More specifically, a rabbit anti-human IgG antibody is immobilized as a sensing substance on the surface of a thin film layer, and a human IgG antibody is used as a specific substance.

It is to be noted that in order to measure a binding state between a test substance and a sensing substance, it is not always necessary to detect the angle itself of an attenuated total reflection angle ($\theta SP$). For example, a sample solution may be added to a sensing substance, and the amount of an attenuated total reflection angle ($\theta SP$) changed thereby may be measured, so that the binding state can be measured based on the magnitude by which the angle has changed. When the above-described array-form light-detecting means and differentiating means are applied to a measurement device using attenuated total reflection, the amount by which a derivative value has changed reflects the amount by which the attenuated total reflection angle ($\theta SP$) has changed. Accordingly, based on the amount by which the derivative value has changed, a binding state between a sensing substance and a test substance can be measured (Japanese Patent Application No. 2000-398309 filed by the present applicant). In a measuring method and a measurement device using such attenuated total reflection, a sample solution consisting of a solvent and a test substance is added dropwise to a cup- or petri dish-shaped measurement chip wherein a sensing substance is immobilized on a thin film layer previously formed at the bottom, and then, the above-described amount by which an attenuated total reflection angle (θSP) has changed is measured.

Moreover, Japanese Patent Laid-Open No. 2001-330560 describes a measurement device using attenuated total reflection, which involves successively measuring multiple measurement chips mounted on a turntable or the like, so as to measure many samples in a short time.

When the biosensor of the present invention is used in surface plasmon resonance analysis, it can be applied as a part of various surface plasmon measurement devices described above.

The present invention will be further specifically described in the following examples. However, the examples are not intended to limit the scope of the present invention.

EXAMPLES

The device described in FIG. 1 (the surface plasmon resonance measurement device of the present invention) was used in experiments. The detailed descriptions of the device shown in FIG. 1 are found in Japanese Patent Application Laid-Open (Kokai) No. 2003-254906. Evaluation of a two-part split surface and measurement with two cups were carried out under the same conditions by adjusting the width of an optical path after a beam splitter.

Example A:

Example A-1:

Production of Measurement Chip (the Present Invention)

(1) Production of Polymethyl Methacrylate (PMMA) Film

A dielectric block onto which gold with a thickness of 50 nm had been evaporated as a metal film was treated with a Model-208 UV-ozone cleaning system (TECHNOVISION INC.) for 30 minutes. Thereafter, 5 µl of a methyl ethyl ketone solution containing 1 mg/ml polymethyl methacrylate was added thereto such that it came into contact with the metal film. It was left at rest at 25° C. for 15 minutes.

(2) Production of Measurement Chip by Treating Polymethyl Methacrylate Film with NaOH 1 N NaOH aqueous solution was added to the sample produced in (1) above, such that it came into contact with the PMMA film. It was left at rest at 60° C. for 5 hours. Thereafter, it was washed with water 3 times. This sample is called a PMMA/NaOH treated chip.

(3) Production of Two-Part Split Surface

100 µl of a mixed solution consisting of an ethanol solution containing 400 mM 1-ethyl-2,3-dimethylaminopropylcarbodiimide and an ethanol solution containing 100 mM pentafluorophenol at a ratio of 1:1 was added to the sample produced in (2) above. It was left at rest at 25° C. for 30 minutes. Thereafter, it was washed with ethanol 5 times.

Thereafter, a PDMS film having a thickness of 100 µm was allowed to come into contact with the center of the sample as a diaphragm. 20 µl of an ethanol solution containing 1 M ethanolamine was added to one side, and 20 µl of an ethanol solution containing 10 mM biotin-LC-amine (manufactured by PIERCE) was added to the other side. It was then left at rest at 25° C. for 20 minutes. Thereafter, it was washed with ethanol once. The diaphragm was removed, and the resultant sample was washed with ethanol 5 times, with a mixed solvent consisting of ethanol and water once, and then with water 5 times. This sample is called a PMMA two-part split treated chip.

Comparative Example A-1:

Production of Surface that is not Split (1) Production of Surface that is not Split—1 (Reference Unit)

100 µl of a mixed solution consisting of an ethanol solution containing 400 mM 1-ethyl-2,3-dimethylaminopropylcarbodiimide and an ethanol solution containing 100 mM pentafluorophenol at a ratio of 1:1 was added to the sample produced in (2) in Example A-1. It was left at rest at 25° C. for 30 minutes. Thereafter, it was washed with ethanol 5 times. Thereafter, 20 µl of an ethanol solution containing 1 M ethanolamine was added thereto, and it was then left at rest at 25° C. for 20 minutes. Thereafter, it was washed with ethanol 5 times, with a mixed solvent consisting of ethanol and water once, and then with water 5 times. This sample is called a PMMA/reference treated chip.

(2) Production of Surface that is not Split—2 (Measurement Unit)

100 µl of a mixed solution consisting of an ethanol solution containing 400 mM 1-ethyl-2,3-dimethylaminopropylcarbodiimide and an ethanol solution containing 100 mM pentafluorophenol at a ratio of 1:1 was added to the sample produced in (2) in Example A-1. It was left at rest at 25° C. for 30 minutes. Thereafter, it was washed with ethanol 5 times. Thereafter, 20 µl of an ethanol solution containing 10 mM biotin-LC-amine (manufactured by PIERCE) was added thereto, and it was left at rest at 25° C. for 20 minutes. Thereafter, it was washed with ethanol 5 times, with a mixed solvent consisting of ethanol and water once, and then with water 5 times. This sample is called a PMMA/measurement treated chip.

Example A-2:

Production of Two-Part Split Surface by Contact

A stamp used to come into contact with a half portion of the measurement unit of an dielectric block used in measurement was produced from PDMS. The surface thereof was treated with plasma ozone, so as to ensure the wetting properties of the solution.

100 µl of a mixed solution consisting of an ethanol solution containing 400 mM 1-ethyl-2,3-dimethylaminopropylcarbodiimide and an ethanol solution containing 100 mM pentafluorophenol at a ratio of 1:1 was added to the sample produced in (2) in Example A-1. It was left at rest at 25° C. for 30 minutes. Thereafter, it was washed with ethanol 5 times. Thereafter, a stamp that had been immersed in an ethanol solution containing 10 mM biotin-LC-amine (manufactured by PIERCE) was allowed to come into contact with the sample for 20 minutes. Thereafter, the stamp was removed from the sample, and 40 µl of an ethanol solution containing 1 M ethanolamine was added thereto, and it was left at 25° C. for 20 minutes. Thereafter, it was washed with ethanol once. The diaphragm was then removed, and the resultant sample was washed with ethanol 5 times, with a mixed solvent consisting of ethanol and water once, and then with water 5 times. This sample is called a PMMA contact treated chip.

Test Example A:

(1) Evaluation of Two-Part Split Surface (Baseline Measurement—1)

Both the PMMA two-part split treated chip and the PMMA contact treated chip were measured under the following conditions.

An HBS-EP solution containing 1%-by-weight DMSO (dimethyl sulfoxide) was added to each chip, and the baseline was measured for 30 minutes. It is to be noted that the composition of the HBS-EP solution consisted of 0.01 mol/l HEPES (N-2-hydroxyethylpiperazin-N'-2-ethanesulfonic acid) (pH 7.4), 0.15 mol/l NaCl, 0.003 mol/l EDTA, and 0.005%-by-weight Surfactant P20.

The difference between the reference unit and the measurement unit was obtained, and the fluctuation width (the width made between the maximum and the minimum) was defined as $\Delta T$. As the value of $\Delta T$ is close to 0, measurement can be carried out with good precision.

(2) Evaluation of the Two Cup Method (Baseline Measurement—2)

While the PMMA/reference treated chip and the PMMA/measurement treated chip were simultaneously measured, the measurement was carried out by the same method as described in (1) above.

(3) Evaluation of Two-Part Split Surface (Nonspecific Adsorption Measurement—1)

100 µl of an HBS-EP solution containing 1%-by-weight DMSO (dimethyl sulfoxide) was added to the chip, and the baseline was measured for 1 minute. The obtained point was defined as a start point. Thereafter, the liquid was exchanged, and an HBS-EP solution containing 100 µg/ml bovine serum albumin (HBS-EP solution) and 1%-by-weight DMSO (dimethyl sulfoxide) was measured. After it was left for 15 minutes, the obtained point was defined as an end point, and the measurement was terminated.

After the value of the measurement face and the value of the reference face were subtracted, the value of the start point was subtracted from the value of the end point. The obtained value was defined as NSB. Since the measurement face the surface of which was modified with a biotin derivative did not interact with bovine serum albumin, the value of NSB is preferably close to 0.

(4) Evaluation of the Two Cup Method (Nonspecific Adsorption Measurement—2)

While the PMMA/reference treated chip and the PMMA/measurement treated chip were simultaneously measured, the measurement was carried out by the same method as described in (3) above.

(5) Evaluation of Two-Part Split Surface (Binding Measurement—1)

100 µl of an HBS-EP solution containing 1%-by-weight DMSO (dimethyl sulfoxide) was added to the chip, and the baseline was measured for 1 minute. The obtained point was defined as a start point. Thereafter, the liquid was exchanged, and an HBS-EP solution containing 0.1 µg/ml avidin, 100 µg/ml bovine serum albumin, and 1%-by-weight DMSO (dimethyl sulfoxide) was measured. After it was left for 15 minutes, the obtained point was defined as an end point, and the measurement was terminated.

After the value of the measurement face and the value of the reference face were subtracted, the value of the start point was subtracted from the value of the end point. The obtained value was defined as BIND.

(6) Evaluation of the Two Cup Method (Binding Measurement—2)

While the PMMA/reference treated chip and the PMMA/measurement treated chip were simultaneously measured, the measurement was carried out by the same method as described in (5) above.

(7) Evaluation Results

The results of the measurements described in (1) to (6) above are shown in Table 1.

TABLE 1

| | | $\Delta T$ (RU) | NSB (RU) | BIND (RU) | Remarks |
|---|---|---|---|---|---|
| Measurement with surface two-part split chip | PMMA two-part split surface | 1 RU | 5 RU | 950 RU | Example 1 (the present invention) |
| | PMMA contact treated chip | 1 RU | 250 RU | 1,425 RU | Example 2 (the present invention) |
| Measurement with two chips | Measurement chip/reference chip | 10 RU | 15 RU | 945 RU | Comparative example 1 |

As is clear from the results shown in Table 1, in the case of the measurement with two cups, the baseline fluctuation that should originally be 0 increases, and thus, it cannot be used in precision measurement. In addition, if a two-part split surface is produced by contact, the thin film placed on gold is destroyed, and the gold surface appears, thereby leading to deterioration in nonspecific adsorption. Thus, the value caused by such nonspecific adsorption is added to the actual binding value, and this results in a decrease in measurement precision. In contrast, when a two-part split surface is produced by a non-contact method according to the method of the present invention, the baseline fluctuation is small, and nonspecific adsorption can be suppressed.

Example B:

Example B-1:

Production of Chip for Biosensors (1) Production of Chip for Biosensors Coated with Polymethyl Methacrylate A cover glass with a size of 1 cm×1 cm, onto which gold had been evaporated resulting in a gold film with a thickness of 500 angstroms, was treated with a Model-208 UV-ozone cleaning system (TECHNOVISION INC.) for 30 minutes. Thereafter, the cover glass was placed in a spin coating machine (MODEL ASS-303, manufactured by ABLE), and it was then rotated at 1,000 rpm. 50 µl of a methyl ethyl ketone solution containing polymethyl methacrylate (2 mg/ml) was added dropwise to the center of the cover glass coated with gold via evaporation. After 2 minutes, the rotation was terminated. The thickness of the film was measured by ellipsometry (In-Situ Ellipsometer MAUS-101, manufactured by Five Lab). As a result, the thickness of the polymethyl methacrylate film was found to be 200 angstroms. This sample is called a PMMA surface chip.

(2) Introduction of COOH Group onto PMMA Surface

The above produced cover glass coated with polymethyl methacrylate was immersed in an NaOH aqueous solution (1N) at 40° C. for 16 hours, and it was then washed with water 3 times. This sample is called a PMMA/COOH surface chip.

(3) Production of Surface having Linker—1 (Comparative Example)

The PMMA/COOH surface chip produced in (2) above was immersed in 2 ml of a mixed solution consisting of 1-ethyl-2,3-dimethylaminopropylcarbodiimide (400 mM) and N-hydroxysuccinimide (100 mM) for 60 minutes. Thereafter, it was immersed in 2 ml of an ethylenediamine aqueous solution (10 mM) for 16 hours. Finally, it was washed with water 5 times. This sample is called a PMMA/Eda surface chip.

(4) Production of Surface having Linker—2 (Comparative Example)

The PMMA/COOH surface chip produced in (2) above was immersed in 2 ml of a mixed solution consisting of 1-ethyl-2,3-dimethylaminopropylcarbodiimide (400 mM) and N-hydroxysuccinimide (100 mM) for 60 minutes. Thereafter, it was immersed in 2 ml of a 5-aminovaleric acid solution (10 mM) for 16 hours. Finally, it was washed with water 5 times. This sample is called a PMMA/Val surface chip.

(5) Production of Surface having Linker—3 (the Present Invention)

The PMMA/COOH surface chip produced in (2) above was immersed in 2 ml of a mixed solution consisting of 1-ethyl-2,3-dimethylaminopropylcarbodiimide (400 mM) and N-hydroxysuccinimide (100 mM) for 60 minutes. Thereafter, it was immersed in 2 ml of an aqueous solution (10 mM) of an α-amino-polyethyleneoxy-ω-carboxylic acid (mean molecular weight: 5,000) for 16 hours. Finally, it was washed with water 5 times. This sample is called a PMMA/PEO-C surface chip.

(6) Production of Surface having Linker—4 (the Present Invention)

The PMMA/COOH surface chip produced in (2) above was immersed in 2 ml of a mixed solution consisting of 1-ethyl-2,3-dimethylaminopropylcarbodiimide (400 mM) and N-hydroxysuccinimide (100 mM) for 60 minutes. Thereafter, it was immersed in 2 ml of a solution (10 mM) of diamino polyethylene glycol (mean molecular weight: 5,000) for 16 hours. Finally, it was washed with water 5 times. This sample is called a PMMA/PEO-A5 surface chip.

(7) Production of Surface having Linker—5 (the Present Invention)

The PMMA/COOH surface chip produced in (2) above was immersed in 2 ml of a mixed solution consisting of 1-ethyl-2,3-dimethylaminopropylcarbodiimide (400 mM) and N-hydroxysuccinimide (100 mM) for 60 minutes. Thereafter, it was immersed in 2 ml of a solution (10 mM) of diamino polyethylene glycol (mean molecular weight: 10,000) for 16 hours. Finally, it was washed with water 5 times. This sample is called a PMMA/PEO-A10 surface chip.

Example B-2:

Evaluation of Performance of Chip for Biosensors (1) Immobilization of Protein

Each chip shown in the following samples 1-1 to 1-5 was placed on the cartridge block of a commercially available surface plasmon resonance biosensor (manufactured by Biacore K. K., BIACORE 3000), and trypsin (manufactured by Nacalai Tesque) was immobilized thereon. The amount of trypsin immobilized was used as a coefficient for the following comparison of enzyme activity.

Sample 1-1: PMMA/Eda surface chip (produced by the method described in Example B-1 (3))
Sample 1-2: PMMA/Val surface chip (produced by the method described in Example B-1 (4))
Sample 1-3: PMMA/PEO-C surface chip (produced by the method described in Example B-1 (5))
Sample 1-4: PMMA/PEO-A5 surface chip (produced by the method described in Example B-1 (6))
Sample 1-5: PMMA/PEO-A10 surface chip (produced by the method described in Example B-1 (7))

Method (A) was applied to samples 1-2 and 1-3, and Method (B) was applied to samples 1-1, 1-4, and 1-5.

Method (A)

150 μl of a mixed solution consisting of 1-ethyl-2,3-dimethylaminopropylcarbodiimide (400 mM) and N-hydroxysuccinimide (100 mM) was fed to a measuring cell at a flow rate of 10 μl/min. Thereafter, 150 μl of a solution (acetate buffer, pH 5.5) of 0.1 mg/ml trypsin (manufactured by Nacalai Tesque) was fed to the measuring cell at a flow rate of 10 μl/min. Thereafter, 150 μl of an ethanolamine/HCl solution (1 M, pH 8.5) was fed to the measuring cell at a flow rate of 10 μl/min. Subsequently, 10 μl of a 10 mM NaOH aqueous solution was fed to the measuring cell twice at a flow rate of 10 μl/min. to wash the cell, so as to eliminate trypsin that had not covalently bound. Before and after each of the above solutions was poured to the measuring cell, an HBS-EP buffer (manufactured by Biacore K.K., pH 7.4) (which consisted of: 0.01 mol/l HEPES (pH 7.4); 0.15 mol/l NaCl; 0.003 mol/l EDTA; and 0.005%-by-weight Surfactant P20) was fed thereto at a flow rate of 10 μl/min.

Method (B)

150 μl of an aqueous solution of compound A (500 mM) was fed to a measuring cell at a flow rate of 10 μl/min. Thereafter, 150 μl of a solution (acetate buffer, pH 5.5) of 0.1 mg/ml trypsin (manufactured by Nacalai Tesque) was fed to the measuring cell at a flow rate of 10 μl/min. Thereafter, 150 μl of an ethanolamine/HCl solution (1 M, pH 8.5) was fed to the measuring cell at a flow rate of 10 μl/min. Subsequently, 10 μl of a 10 mM NaOH aqueous solution was fed to the measuring cell twice at a flow rate of 10 μl/min. to wash the cell, so as to eliminate trypsin that had not covalently bound. Before and after each of the above solutions was poured to the measuring cell, an HBS-EP buffer (manufactured by Biacore K.K., pH 7.4) (which consisted of: 0.01 mol/l HEPES (pH 7.4); 0.15 mol/l NaCl; 0.003 mol/l EDTA; and 0.005%-by-weight Surfactant P20) was fed thereto at a flow rate of 10 μl/min.

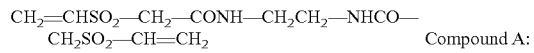

$$CH_2=CHSO_2-CH_2-CONH-CH_2CH_2-NHCO-CH_2SO_2-CH=CH_2 \qquad \text{Compound A:}$$

The value obtained before pouring the agent was defined as 0, and the value obtained after washing with an NaOH solution was defined as the amount of trypsin immobilized. Using these values, the value of enzyme activity described later was calculated.

(2) Measurement of Enzyme Activity

The chip which was subjected to immobilization in (1) above was directly used, and the following measurement was carried out.

The surface of the chip was washed 3 times with 0.05 M Tris HCl (pH 8.0, 0.02 M $CaCl_2$). Thereafter, 100 μl of a solution of 0.1 mM Bz-Arg-MCA (Peptide Institute, Inc.) was placed on the chip. 120 minutes later, the total amount was transferred onto a measurement plate, and fluorescence measurement was then carried out at a detection wavelength of 460 nm (excitation wavelength: 380 nm) with FLUOstar (BMG Labtechnologies GmbH). The value obtained by dividing the measurement value by the amount of trypsin immobilized (RU) was defined as an enzyme activity value.

(3) Results

The results regarding enzyme activity values are shown in Table 2.

TABLE 2

| | Enzyme activity value | Remarks |
|---|---|---|
| Sample 1-1 | 0.05 | Comparative example |
| Sample 1-2 | 0.05 | Comparative example |
| Sample 1-3 | 0.11 | The present invention |
| Sample 1-4 | 0.09 | The present invention |
| Sample 1-5 | 0.10 | The present invention |

From the results shown in Table 2, it is found that with the structure of the present invention, a surface with a large enzyme activity value can be provided.

Example C:

Example C-1:

Production of Chip for Biosensors (1) Production of Chip for Biosensors Coated with Polymethyl Methacrylate A cover glass with a size of 1 cm×1 cm, onto which gold had been evaporated resulting in a gold film with a thickness of 500 angstroms, was treated with a Model-208 UV-ozone cleaning system (TECHNOVISION INC.) for 30 minutes. Thereafter, the cover glass was placed in a spin coating machine (MODEL ASS-303, manufactured by ABLE), and it was then rotated at 1,000 rpm. 50 μl of a methyl ethyl ketone solution containing polymethyl methacrylate (2 mg/ml) was added dropwise to the center of the cover glass coated with gold via evaporation. After 2 minutes, the rotation was terminated. The thickness of the film was measured by ellipsometry (In-Situ Ellipsometer MAUS-101, manufactured by Five Lab). As a result, the thickness of the polymethyl methacrylate film was found to be 200 angstroms. This sample is called a PMMA surface chip.

(2) Introduction of COOH Group onto PMMA Surface

The above produced cover glass coated with polymethyl methacrylate was immersed in an NaOH aqueous solution (1N) at 40° C. for 16 hours, and it was then washed with water 3 times. This sample is called a PMMA/COOH surface chip.

(3) Production of Surface having Linker—1

The PMMA/COOH surface chip produced in (2) above was immersed in 2 ml of a mixed solution consisting of 1-ethyl-2,3-dimethylaminopropylcarbodiimide (400 mM) and N-hydroxysuccinimide (100 mM) for 60 minutes. Thereafter, it was immersed in 2 ml of an ethylenediamine aqueous solution (10 mM) for 16 hours. Finally, it was washed with water 5 times. This sample is called a PMMA/Eda surface chip.

(4) Production of Surface having Linker—2

The PMMA/COOH surface chip produced in (2) above was immersed in 2 ml of a mixed solution consisting of 1-ethyl-2,3-dimethylaminopropylcarbodiimide (400 mM) and N-hydroxysuccinimide (100 mM) for 60 minutes. Thereafter, it was immersed in 2 ml of a solution (10 mM) of six-arm poly(ethylene oxide)amino terminated (mean molecular weight: 12,000; manufactured by Polymer Source) having the structure indicated below for 16 hours. Finally, it was washed with water 5 times. This sample is called a PMMA/PEO-A6 surface chip.

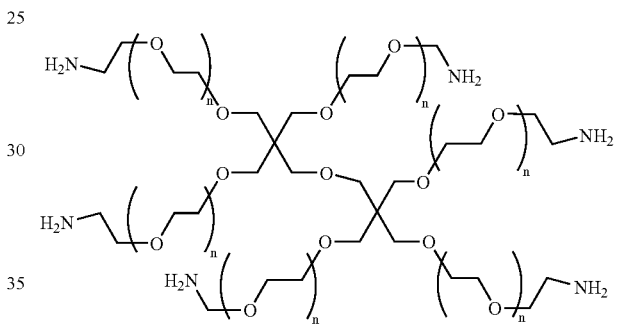

(5) Production of Surface having Linker—3

The PMMA/COOH surface chip produced in (2) above was immersed in 2 ml of a mixed solution consisting of 1-ethyl-2,3-dimethylaminopropylcarbodiimide (400 mM) and N-hydroxysuccinimide (100 mM) for 60 minutes. Thereafter, it was immersed in 2 ml of a solution (10 mM) of four-arm poly(ethylene oxide)amino terminated (mean molecular weight: 10,000; manufactured by Polymer Source) having the structure indicated below for 16 hours. Finally, it was washed with water 5 times. This sample is called a PMMA/PEO-A4 surface chip.

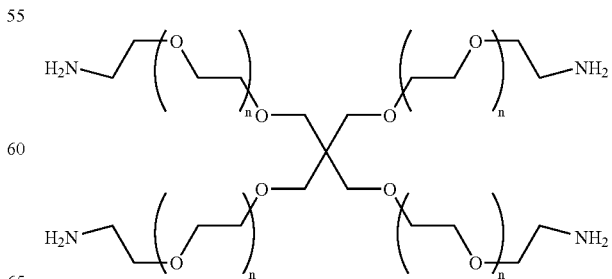

Example C-2:

Evaluation of Performance of Chip for Biosensors (1) Immobilization of Protein

Each chip shown in the above samples 1-1 to 1-6 was placed on the cartridge block of a commercially available surface plasmon resonance biosensor (manufactured by Biacore K. K., BIACORE 3000), and trypsin (manufactured by Nacalai Tesque) was immobilized. The amount of trypsin immobilized was used as a coefficient for the following comparison of enzyme activity.

Sample 1-1: PMMA/COOH surface chip (produced by the method described in Example C-1 (2))

Sample 1-2: PMMA/Eda surface chip (produced by the method described in Example C-1 (3))

Sample 1-3: PMMA/PEO-A6 surface chip (produced by the method described in Example C-1 (4))

Sample 1-4: PMMA/PEO-A4 surface chip (produced by the method described in Example C-1 (5))

The following immobilization method was used.

150 μl of an aqueous solution of compound A (500 mM) was fed to a measuring cell at a flow rate of 10 μl/min. Thereafter, 150 μl of a solution (acetate buffer, pH 5.5) of 0.1 mg/ml trypsin (manufactured by Nacalai Tesque) was fed to the measuring cell at a flow rate of 10 μl/min. Thereafter, 150 μl of an ethanolamine/HCl solution (1 M, pH 8.5) was fed to the measuring cell at a flow rate of 10 μl/min. Subsequently, 10 μl of a 10 mM NaOH aqueous solution was fed to the measuring cell twice at a flow rate of 10 μl/min. to wash the cell, so as to eliminate trypsin that had not covalently bound. Before and after each of the above solutions was poured to the measuring cell, an HBS-EP buffer (manufactured by Biacore K.K., pH 7.4) (which consisted of: 0.01 mol/l HEPES (pH 7.4); 0.15 mol/l NaCl; 0.003 mol/l EDTA; and 0.005%-by-weight Surfactant P20) was fed thereto at a flow rate of 10 μl/min.

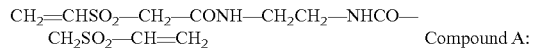

$CH_2=CHSO_2-CH_2-CONH-CH_2CH_2-NHCO-CH_2SO_2-CH=CH_2$    Compound A:

The value obtained before pouring the agent was defined as 0, and the value obtained after washing with an NaOH solution was defined as the amount of trypsin immobilized. Using these values, the value of enzyme activity described later was calculated.

(2) Measurement of Enzyme Activity

The chip immobilized in (1) above was directly used, and the following measurement was carried out.

The surface of the chip was washed 3 times with 0.05 M Tris HCl (pH 8.0, 0.02 M $CaCl_2$). Thereafter, 100 μl of a solution of 0.1 mM Bz-Arg-MCA (Peptide Institute, Inc.) was placed on the chip. 120 minutes later, the total amount was transferred onto a measurement plate, and fluorescence measurement was then carried out at a detection wavelength of 460 nm (excitation wavelength: 380 nm) with FLUOstar (BMG Labtechnologies GmbH). The value obtained by dividing the measurement value by the amount of trypsin immobilized (RU) was defined as an enzyme activity value.

(3) Results

The results regarding the amounts of trypsin immobilized and the enzyme activity values are shown in Table 3.

TABLE 3

|  | Enzyme activity value | Remarks |
| --- | --- | --- |
| Sample 1-1 | 0.05 | Comparative example |
| Sample 1-2 | 0.05 | Comparative example |
| Sample 1-3 | 0.13 | The present invention |
| Sample 1-4 | 0.12 | The present invention |

From the results shown in Table 3, it is found that with the structure of the present invention, a surface with a large enzyme activity value can be provided.

Example D:

Example D-1

(1) Production of Measurement Chip of the Present Invention (1-1) Production of Polymethyl Methacrylate (Hereinafter Referred to as PMMA) Film The dielectric block of the present invention onto which gold with a thickness of 50 nm had been evaporated was treated with a Model-208 UV-ozone cleaning system (TECHNOVISION INC.) for 30 minutes. Thereafter, 5 μl of a methyl ethyl ketone solution containing 1 mg/ml polymethyl methacrylate was added thereto such that it came into contact with the metal film. It was left at rest at 25° C. for 15 minutes. The thickness of the obtained PMMA film was 20 nm.

(1-2) Hydrolytic Treatment of PMMA Film

1 N NaOH aqueous solution was added to the aforementioned PMMA film, such that it came into contact with the film. It was left at rest at 60° C. for 5 hours. Thereafter, it was washed with water 3 times. A carboxyl group was introduced onto the surface of the PMMA film by this treatment.

(1-3) Activation of Carboxyl Group

An ethanol solution containing 400 mM 1-ethyl-2,3-dimethylaminopropylcarbodiimide was mixed with an ethanol solution containing 100 mM pentafluorophenol at a ratio of 1:1. 100 μl of the mixed solution was allowed to come into contact with the surface of the aforementioned PMMA film onto which a carboxyl group had been introduced. It was left at rest at 25° C. for 30 minutes. Thereafter, it was washed with ethanol 5 times.

(1-4) Patterning by Using Ink-Jet Printing (the Present Invention)

Using an ink-jet device equipped with a nozzle head for delivering 12-picoliter ink droplet with 180 dpi resolution (manufactured by Seiko Instruments), an ethanol solution of 10 mM biotin-LC-amine (manufactured by PIERCE) was applied by ink-jet printing to a half portion of the surface of the aforementioned PMMA film onto which an activated carboxyl group had been introduced. The biotin-LC-amine used herein corresponds to the linker for immobilizing a physiologically active substance in the present invention. In addition, introduction of the linker into only a half portion of the PMMA film corresponds to patterning in the present invention.

(1-5) Blocking

40 μl of an ethanol solution of 1 M ethanolamine was allowed to come into contact with the entire surface of the PMMA film obtained in (2-4) above, and it was then left at 25° C. for 20 minutes. Thereafter, it was washed with ethanol 5 times, with a mixed solvent consisting of ethanol and water once, and then with water 5 times.

(2) Production of Measurement Chip of Comparative Example

A measurement chip was produced in the same manner as in the production of the aforementioned measurement chip of the present invention with exception that the patterning of a linker described in (1-4) above was changed to the following method, so as to obtain the measurement chip of comparative example.

(2-1) Patterning Using Stamp (Comparative Example)

A stamp that is allowed to come into contact with a half portion of the measurement unit of an dielectric block used in measurement was produced from PDMS. The surface thereof was treated with plasma ozone, so as to ensure hydrophilicity. This stamp was immersed in an ethanol solution of 10 mM biotin-LC-amine (manufactured by PIERCE) for 1 minute. Thereafter, the stamp was pressed for 20 minutes against a half portion of the surface of the PMMA film described in (1-3) above, onto which an activated carboxyl group had been introduced.

(3) Evaluation of Measurement Chip

Each of the measurement chips of the present invention and comparative example, which were produced in (1) and (2) above was equipped in the surface plasmon resonance device shown in FIG. 1, and a biotinylated IL-8 antibody (manufactured by Techne) was immobilized thereon by the following procedures.

(3-1) Immobilization of Biotinylated IL-8 Antibody

100 µl of an HBS—N buffer (pH 7.4, manufactured by Biacore K. K.) was added, so that the obtained value was defined as a baseline. The composition of the HBS—N buffer consisted of 0.01 mol/l HEPES (N-2-hydroxyethylpiperazin-N'-2-ethanesulfonic acid) (pH 7.4) and 0.15 mol/l NaCl. Subsequently, the buffer was replaced with 100 µl of a biotinylated IL-8 antibody solution (50 µl/ml, HBS—N buffer (pH 7.4)), and it was then left at rest for 10 minutes. Thereafter, it was washed with 100 µl of an HBS—N buffer. The amount by which the resonance signal (RU value) had changed from the baseline was defined as the amount of the biotinylated IL-8 antibody immobilized (RU value). In addition, the concentration of the biotinylated IL-8 antibody solution was adjusted to be 500 µg/ml, and the same immobilization operation was carried out.

(3-2) Reproduction of the Amount of Biotinylated IL-8 Antibody Immobilized 20 measurement chips of the present invention and 20 measurement chips of comparative example were prepared. The amount of a biotinylated IL-8 antibody immobilized was measured by the aforementioned method. The mean value and the CV value were calculated. The CV value was calculated herein by the following formula:

$CV$ value (%)=(standard deviation/mean value)×100

(3-3) Measurement of Binding Amount of IL-8

Using the measurement chips of the present invention and comparative example, on which the aforementioned biotinylated IL-8 antibody had been immobilized, the binding amount of human IL-8 (manufactured by Pepro Tech EC) was measured. First, 100 µl of an HBS—N buffer (pH 7.4, manufactured by Biacore K. K.) was added, so that the obtained value was defined as a baseline. Thereafter, the buffer was replaced with 100 µl of an IL-8 antibody solution (10 ng/ml, HBS—N buffer (pH 7.4)), and it was then left at rest for 10 minutes. Thereafter, it was washed with 100 µl of an HBS—N buffer. The amount by which the resonance signal (RU value) had changed from the baseline was defined as the amount of the IL-8 bound (RU value).

(3-4) Reproduction of the Binding Amount of IL-8

Using 20 measurement chips of the present invention and 20 measurement chips of comparative example produced in (3-2) above, on which a biotinylated IL-8 antibody had been immobilized, the binding amount of IL-8 was measured by the method described in (3-3) above. The mean value and the CV value were calculated.

(Evaluation Results)

Evaluation results are shown in Table 4.

TABLE 4

| Experiment No. | Patterning method | Concentration of biotinylated IL-8 antibody (µg/ml) | Immobilization of biotinylated IL-8 antibody | | Binding of IL-8 | | Remarks |
|---|---|---|---|---|---|---|---|
| | | | Mean value of amount immobilized (RU) | CV value of amount immobilized (%) | Mean value of amount bound (RU) | CV value of amount bound (%) | |
| 1 | Stamp | 50 | 1,320 | 25% | Below detection limit | — | Comparative example |
| 2 | Stamp | 500 | 4,650 | 19% | 15 RU | 30% | Comparative example |
| 3 | Ink-jet printing | 50 | 5,310 | 5% | 29 RU | 9% | The present invention |
| 4 | Ink-jet printing | 500 | 6,890 | 3% | 34 RU | 6% | The present invention |

From the results shown in Table 4, it is found that with the structure of the present invention, even using an antibody solution with a low concentration, an antibody-immobilized surface having good detectability of antigen binding can be provided. Moreover, it is found that the measurement chip produced by the present invention is extremely good in terms of the reproducibility of the amount of an antibody immobilized and the amount of antigen bound.

EFFECTS OF THE INVENTION

The present invention provides a detection surface used for biosensors, which is not significantly affected by the baseline fluctuation and suppresses nonspecific adsorption. The present invention provides a detection surface used for biosensors, which is capable of immobilizing all types of physiologically active substances stably, that is, while suppressing decreases in the original activities of the physiologically active substances. The present invention provides a biosensor: which can favorably detect the binding of a physiologically active substance with a substance interacting therewith even when the physiologically active substance is immobilized on the biosensor using a solution containing a low concentration of the physiologically active substance; and which causes a low variation in the binding amount of the physiologically substance and in the binding amount of the substance interacting therewith.

The invention claimed is:

1. A biosensor comprising a substrate which is coated with a hydrophobic polymer, to the surface of which a hydrophilic compound binds, and wherein the hydrophobic polymer is formed with a hydrophobic monomer selected from the group consisting of vinyl esters, acrylic esters, methacrylic esters, olefins, styrenes, crotonic esters, itaconic diesters, maleic diesters, fumaric diesters, allyl compounds, vinyl ethers and vinyl ketones.

2. The biosensor according to claim 1, wherein the molecular weight of the hydrophilic compound is between 50 and 20,000.

3. The biosensor according to claim 1, wherein one group capable of binding to one molecule of a physiologically active substance exists in one molecule of the hydrophilic compound.

4. The biosensor according to claim 1, wherein 2 to 1,000 groups binding to a physiologically active substance exist in one molecule of the hydrophilic compound.

5. The biosensor according to claim 1, wherein the hydrophilic compound is gelatin, alginic acid, chitosan, dextran, polyvinyl alcohol, polyethylene glycol or a derivative thereof, carrageenan, agarose, polyacrylic acid, or polyacrylamide.

6. A method for producing the biosensor according to claim 1, which comprises steps of coating the substrate with the hydrophobic polymer, and allowing a hydrophilic compound to bind to the hydrophobic polymer coated on the substrate.

7. The biosensor according to claim 1, wherein a physiologically active substance is bound to the surface by covalent bonding.

8. A method for immobilizing a physiologically active substance on a biosensor, which comprises a step of allowing a physiologically active substance to come into contact with the biosensor according to claim 1, so as to allow said physiologically active substance to bind to the surface of said biosensor via a covalent bond.

9. A method for detecting or measuring a substance interacting with a physiologically active substance, which comprises a step of allowing a test substance to come into contact with the biosensor according to claim 1 to the surface of which the physiologically active substance binds via a covalent bond and then detecting or measuring the test substance.

10. The method according to claim 9, wherein the substance interacting with the physiologically active substance is detected or measured by a non-electrochemical method.

11. The method according to claim 9, wherein the substance interacting with the physiologically active substance is detected or measured by surface plasmon resonance analysis.

* * * * *